(12) United States Patent
Madabhushi et al.

(10) Patent No.: US 11,461,891 B2
(45) Date of Patent: Oct. 4, 2022

(54) PHENOTYPING TUMOR INFILTRATING LYMPHOCYTES ON HEMATOXYLIN AND EOSIN (HANDE) STAINED TISSUE IMAGES TO PREDICT RECURRENCE IN LUNG CANCER

(71) Applicant: Case Western Reserve University, Cleveland, OH (US)

(72) Inventors: Anant Madabhushi, Shaker Heights, OH (US); Cristian Barrera, Bogota (CO); German Corredor, Bogota (CO); Eduardo Romero, Bogota (CO)

(73) Assignee: Case Western Reserve University, Cleveland, OH (US)

( * ) Notice: Subject to any disclaimer, the term of this patent is extended or adjusted under 35 U.S.C. 154(b) by 866 days.

(21) Appl. No.: 16/263,334

(22) Filed: Jan. 31, 2019

(65) Prior Publication Data
US 2019/0279359 A1    Sep. 12, 2019

Related U.S. Application Data

(60) Provisional application No. 62/639,256, filed on Mar. 6, 2018.

(51) Int. Cl.
*G06K 9/00*  (2022.01)
*G06T 7/00*  (2017.01)
(Continued)

(52) U.S. Cl.
CPC .......... *G06T 7/0012* (2013.01); *G06K 9/6228* (2013.01); *G16B 40/00* (2019.02);
(Continued)

(58) Field of Classification Search
CPC . G06T 2207/20081; G06T 2207/30024; G06T 2207/30061; G06T 2207/30096;
(Continued)

(56) References Cited

U.S. PATENT DOCUMENTS

2017/0193657 A1*  7/2017  Madabhushi ........ G06K 9/6269
2020/0105413 A1*  4/2020  Vladimirova ......... G06T 7/0012
(Continued)

*Primary Examiner* — Atiba O Fitzpatrick
(74) *Attorney, Agent, or Firm* — Eschweiler & Potashnik, LLC

(57) ABSTRACT

Embodiments include controlling a processor to access an image of a region of tissue demonstrating cancerous pathology; segment a cellular nucleus represented in the image; extract a first set of features from the segmented cellular nucleus; classify the segmented nucleus as a lymphocyte or non-lymphocyte based on the first set of features; for a segmented nucleus classified as a lymphocyte: computing a set of contextual features; assign the segmented nucleus classified as a lymphocyte to one of a plurality of clusters based on the set of contextual features; compute a frequency distribution of the clustered segmented nuclei classified as lymphocytes; provide the frequency distribution to a machine learning classifier; receive, from the machine learning classifier, a classification of the region of tissue as likely to experience recurrence or unlikely to experience recurrence, based, at least in part, on the frequency distribution; and display the classification.

20 Claims, 10 Drawing Sheets

(51) Int. Cl.
  *G06K 9/62* (2022.01)
  *G16B 40/00* (2019.01)
(52) U.S. Cl.
  CPC .............. *G06T 2207/10056* (2013.01); *G06T 2207/20081* (2013.01); *G06T 2207/30024* (2013.01); *G06T 2207/30061* (2013.01); *G06T 2207/30096* (2013.01)
(58) Field of Classification Search
  CPC .............................. G06T 7/0012–0016; G06T 2207/30004–30104; G06T 2207/10056–10061; G06T 2207/20084; G06T 2207/30242; G06T 7/10–194; G06T 2207/20112; G16B 40/00; G06K 9/6228; G06K 9/6217; G06K 9/6218; G06K 9/6224; G16H 50/20; G06V 2201/03; G06V 20/695; G06V 40/162; G06N 3/08; A61B 8/085; A61B 5/7485
  See application file for complete search history.

(56) References Cited

U.S. PATENT DOCUMENTS

| | | | |
|---|---|---|---|
| 2020/0258223 A1* | 8/2020 | Yip | G06T 11/00 |
| 2021/0027462 A1* | 1/2021 | Bredno | G06V 20/695 |
| 2021/0210205 A1* | 7/2021 | Drake | G16H 50/20 |
| 2022/0101519 A1* | 3/2022 | Yip | G06K 9/6217 |

* cited by examiner

PHENOTYPING TUMOR INFILTRATING LYMPHOCYTES ON HEMATOXYLIN AND EOSIN (HANDE) STAINED TISSUE IMAGES TO PREDICT RECURRENCE IN LUNG CANCER

CROSS REFERENCE TO RELATED APPLICATIONS

This application claims the benefit of U.S. Provisional Application 62/639,256 filed Mar. 6, 2018, which is incorporated by reference herein in its entirety.

FEDERAL FUNDING NOTICE

This invention was made with government support under grants W81XWH-14-1-0323, W81XWH-15-1-0558, W81XWH-16-1-0329 awarded by the Department of Defense, and grants CA199374, CA202752, CA208236, CA216579, CA220581, and RR012463 awarded by the National Institutes of Health. The government has certain rights in the invention.

BACKGROUND

A high density of tumor infiltrating lymphocytes (TILs) is correlated with a better prognosis for many different types of cancer. Spatial interplay between different subtypes of TILs (e.g., CD3, CD4, CD8) may be prognostic of disease outcome. A challenge with existing approaches to TIL subtyping is that they rely on quantitative immunofluorescence (QIF) or immunohisto-chemistry (IHC), which are both complex, tissue-destructive technologies.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
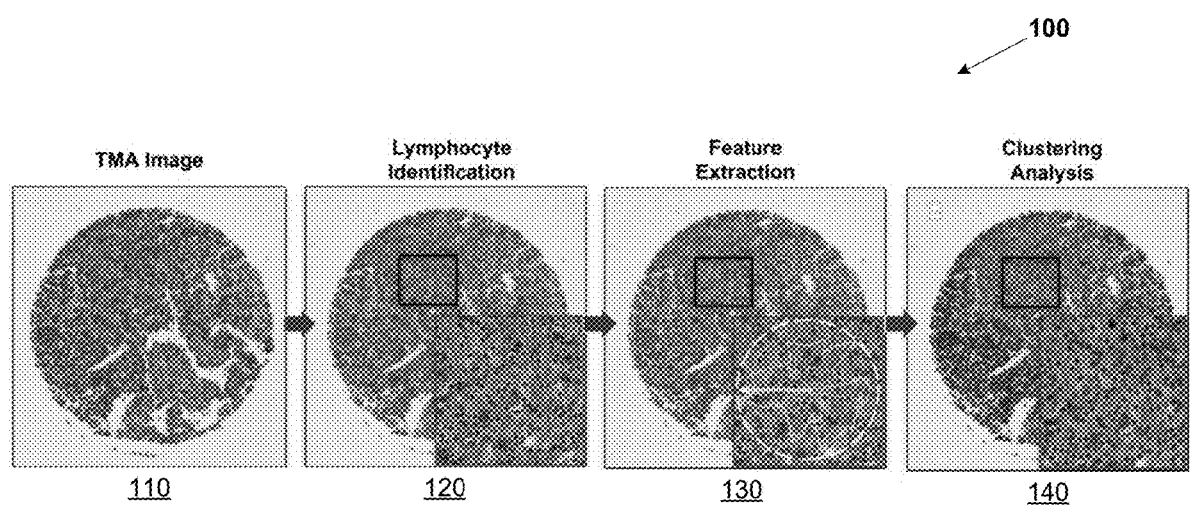
FIG. 1 is a diagram of an exemplary workflow for phenotyping tumor infiltrating lymphocytes (TILs).

In cancer, a tumor may trigger an immune response modulated by tumor-infiltrating lymphocytes (TILs). The density of TILs in tissue is correlated with disease progression, patient survival, and treatment response in different types of cancer, including lung cancer. However, existing immune infiltration metrics that measure TIL density are not as effective in predicting recurrence as evaluating the relative concentrations of different TIL subtypes, each of which may have different biological roles in tumor control. For example, while some TIL populations stimulate an anti-tumor response, others promote cancer progression. Furthermore, different TIL subtypes are difficult, or even impossible, to detect or identify by manual inspection of hematoxylin and eosin (H&E) stained tissue samples.

Existing approaches for detecting different TIL subtypes in H&E stained tissue samples are complex and tissue-destructive. For instance, existing approaches employ multiplexed quantitative immunofluorescence (QIF) or immunohisto-chemistry (IHC) to identify TIL subtypes, including CD3, CD4, and CD8 TILs. Increased levels of CD3 and CD8 TILs are associated with improved outcome in non-small cell lung cancer (NSCLC). Additionally, the spatial interplay between different families of intratumoral TIL cells is correlated with survival in pancreatic cancer. Furthermore, the spatial interplay between tumor and regulatory T cells is associated with survival in NSCLC. However, existing approaches to TIL subtyping in identifying increased levels of CD3 and CD8 TILs, quantifying the spatial interplay between different families of intratumoral TILs, or quantifying the spatial interplay between tumor and regulatory T cells, all employ QIF or IHC, and are thus complex, non-trivial, and tissue destructive processes.

Some existing approaches may employ computerized image analysis for quantifying the presence and extent of TILs from H&E images using both QIF and IHC, and for predicting the outcome and response to therapy. These existing approaches either use machine learning techniques, alone, or use handcrafted features, alone. In contrast, embodiments integrate both handcrafted features and a transfer learning-based CNN approach to identify TILs and TIL regions.

Embodiments non-destructively identify TIL cluster families and their spatial architecture represented in routine H&E stained images, obviating the need for more expensive, complex, tissue-destructive techniques like QIF or IHC. Embodiments derive quantitative measurements from the identified TIL cluster families represented in the H&E stained images, and the spatial architecture of the TIL cluster families. Embodiments further predict recurrence in NSCLC based on the derived quantitative measurements with increased accuracy compared to existing approaches.

Embodiments automatically identify and analyze different TIL families from routine H&E images in a reproducible, more accurate, non-tissue-destructive way using a machine vision approach. Embodiments may employ an automated TIL detection technique to detect lymphocytes and non-lymphocytes represented in a routine H&E image. Embodiments compute contextual features with respect to the detected lymphocytes. Embodiments then cluster detected lymphocytes, based at least in part, on the contextual features, to establish a relation between different TIL families.

TIL subpopulations are strategically distributed with respect to tumoral cells, and the spatial location of the TILs may have biological meaning and relevance. Thus, embodiments that analyze the representation of the tumoral relationships take into account the contextual information, i.e., groups of cells rather than merely individual nuclei. Embodiments define a set of context-based features that model the tumor environment and the relationships between lymphocytes and their surrounding cells, including lymphocytes and non-lymphocytes. Embodiments may further extract morphological features associated with the lymphocytes. Embodiments group lymphocytes using a cluster-based approach, which may include a Dirichlet Process Gaussian Mixture Model (DPGMM). The DPGMM clusters the data extracted from the H&E image via a non-parametric Bayesian framework that describes distributions over mixture models with an infinite number of mixture components. Embodiments thus improve over existing approaches since embodiments do not need to make any assumptions about the number of TIL clusters. Rather than explicitly defining the number of TIL clusters that might exist, embodiments performing clustering using a DPGMM approach facilitate a natural aggregation of groups, which removes the need to make explicit assumptions about the number of clusters. Embodiments then characterize the H&E image by generating a frequency distribution of the TIL clusters, which may be represented as a histogram of occurrences of the identified TILs within the particular partition defined by the clusters. Embodiments then provide the frequency distribution to a machine learning classifier, which classifies the region of tissue represented in the H&E image as likely to experience recurrence or unlikely to experience recurrence, based, at least in part, on the frequency distribution. Embodiments may further train a machine learning classifier using the frequency distributions of H&E images in a training set, to predict the likelihood of recurrence in early stage NSCLC patients. Embodiments may further test the machine learning classifier using the frequency distributions of H&E images in a testing set.

An exemplary embodiment for predicting NSCLC recurrence using TIL phenotyping is now described. FIG. 1 illustrates an example workflow 100 for identifying TIL subtypes in a routine H&E image according to embodiments. Workflow 100 includes, at 110, accessing a routine H&E stained tissue microarray (TMA) image of a region of tissue demonstrating cancerous pathology. In this embodiment, a set of H&E stained TMA images of tissue demonstrating early stage NSCLC is accessed. In another embodiment, other, different stain types may be employed.

Workflow 100 also includes, at 120, identifying lymphocytes represented in the image. Nuclei represented in an H&E image are segmented using a watershed-based technique in this embodiment. Embodiments extract a shape feature, a texture feature, or a color feature from the segmented nuclei. A segmented nucleus is classified as either lymphocyte or non-lymphocyte according to a nuclei texture feature, a shape feature, or a color feature. For example, lymphocyte nuclei are distinguished from other cell nuclei by their smaller size, more rounded shape, and darker homogeneous staining.

Workflow 100 also includes, at 130, extracting features that quantify the relationship between TIL families represented in the image. Embodiments characterize a lymphocyte based on the lymphocyte's own morphological features and further by a set of contextual features to describe the lymphocyte and its surroundings (i.e., local neighborhood). Embodiments may extract morphological features or contextual features using a concentric circles approach. For a lymphocyte, a set of circles with incremental radii of k=dL× 10, dL×20, dL×30 pixels are placed at the lymphocyte center, where dL=20 pixels is the average diameter of the detected lymphocytes. Embodiments may define the center of a lymphocyte by, for example, defining the geometric center of the lymphocyte. Embodiments also compute a set of features extracted from within each circle. Embodiments use the set of features to characterize the lymphocyte. In this example, these features may include but are not limited to features that measure the grouping factor of lymphocytes, relative lymphocyte-cellular density, lymphocyte tissular density, variations of the median intensities of lymphocytes, or relative lymphocyte-cellular interspersing.

In embodiments, the set of contextual features may include a sum of the inverse Euclidean distances between a lymphocyte located on the center of the circle and other lymphocytes in the circled area. The set of contextual features may include a ratio between the sum of the area of lymphocytes and the area of non-lymphocytes. The set of contextual features may include a ratio between the sum of the areas of lymphocytes and the eosinophilic tissue area. The set of contextual features may include a ratio between the number of lymphocytes and the number of non-lymphocytes. The set of contextual features may include an average of the squared differences between the median intensities of lymphocytes. The set of contextual features may include a ratio between the area of a convex hull containing all the lymphocytes and a convex hull containing non-lymphocytes. The set of contextual features may include an intersection between the convex hull containing all the lymphocytes and the convex hull containing all the non-lymphocytes. The set of contextual features may include a median of distances from each lymphocyte to a closest non-lymphocyte neighbor. The set of contextual features may include a ratio between the median of the distance between all the lymphocytes and their closest lymphocyte neighbor and the median of the distance between all the non-lymphocytes and their closest non-lymphocyte neighbor. The set of contextual features may include a number of lymphocytes within a convex hull of non-lymphocytes. The set of contextual features may also include a sum of distances between the centered lymphocyte and its non-lymphocytes neighbors. In other embodiments, the set of contextual features may include other, different contextual features or combinations of contextual features. While in this embodiment, contextual features that consider relationships between all the lymphocytes or all the non-lymphocytes in a region, in another embodiment, contextual features that consider a threshold level of lymphocytes or non-lymphocytes may be employed.

Figure 2:
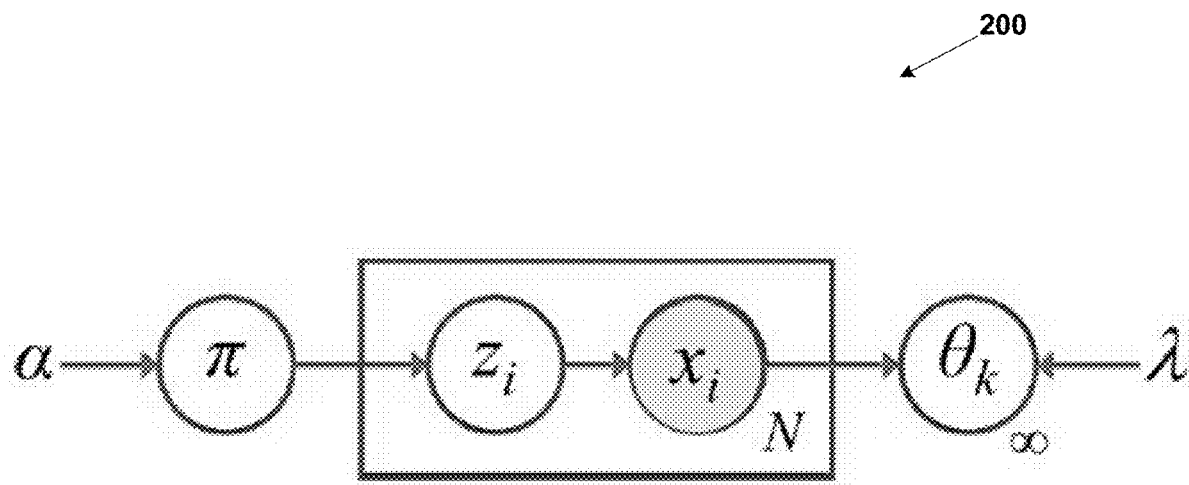
FIG. 2 illustrates a Dirichlet Process Gaussian Mixture Model (DPGMM).

Embodiments perform a clustering analysis of TILs identified in the image. Workflow 100 further includes, at 140, performing a clustering analysis based, at least in part, on the extracted set of morphological or contextual features. Gaussian mixture models are probabilistic models that assume all the data points are generated from a mixture of a finite number of Gaussian distributions with unknown parameters. In such cases, a Dirichlet Process as a prior distribution of the number of clusters, provides that the probability mass can be easily re-distributed. FIG. 2 illustrates an exemplary DPGMM 200 suitable for use by embodiments described herein.

In DPGMM 200, $x_i$ represent observed data points (i.e., individual TILs to be clustered). $Z_i$ represents a set of labels assigning $x_i$ to one of k clusters. Cluster parameters are represented by $\pi$ and $\theta$, where $\pi$ represents mixture proportions, and $\theta$ represents cluster means and covariances. Associated uninformative priors are represented by $\alpha$ and $\lambda$. Since biological subtypes of lymphocytes are not visually distinguishable in H&E images by an unaided human eye or in the human mind, and since it is unknown the number of possible groups existent in a set of H&E images, embodiments that employ DPGMMs facilitate a more convenient framework for TIL clustering than existing approaches.

In this example, it is first assumed that there exists an infinite set of latent groups, each group described by a set of parameters (e.g., a Gaussian with mean $\mu$ and standard deviation $\sigma$). Then, a lymphocyte is assigned to a cluster. One approach suitable for employment by embodiments for assigning a lymphocyte to a cluster is the "stick breaking" approach described herein.

According to the "stick breaking" approach, assume a stick of length one. A random variable $\beta_1 \sim Beta(1, \alpha)$ is generated. A real number between 0 and 1 is set by the Beta distribution, with an expected value of $1/(1+\alpha)$. $\alpha$ is the concentration scaling parameter, and is a positive real number that influences the dispersion of data points. A low $\alpha$ value will generate more tightly clustered data points, while a higher $\alpha$ value will generate more clusters, or a wider range of different clusters. The stick is then broken off at $\beta_1$, and $\omega_1$ is the stick length at the left side. Next, using the right side of the stick, embodiments generate $\beta_2 \sim Beta(1, \alpha)$. The stick is broken off at $\beta_2$, and, as in the previous step, $\omega_2$ is the length of the stick at the left. That is, $\omega_2=(1-\beta_1)/\beta_2$.

Embodiments do not force lymphocytes into specific clusters, or force the creation of specific clusters. Embodiments thus improve on existing approaches that use, for example, K-means clustering, which may force lymphocytes into specific clusters or force the creation of specific clusters. Using the DPGGM, or similar clustering techniques, embodiments ensure that, even if a model discovers, for example, a possible ten top clusters, embodiments are still capable of determining that, for a specific case (e.g., a specific patient) that four of the ten, or three of the ten clusters have been found in the specific case, with specific distribution for each cluster. Embodiments thus facilitate more accurate personalized prediction of recurrence, since the lymphocytes detected in a particular image will be clustered according to the specific properties of that image, and not forced into a specific set of clusters that may not accurately characterize the actual lymphocytes represented in that image.

Embodiments may characterize the image. In this example, once lymphocytes are assigned to a cluster (i.e., group), a histological image may be characterized using the clusters obtained via the DPGMM. A particular image may be represented by a histogram containing the number of TIL occurrences per cluster. These image histograms are normalized, resulting in corresponding probability distribution functions.

Embodiments may train a machine learning classifier to predict the likelihood of recurrence. Embodiments may train the machine learning classifier using a training set. In one embodiment, the training set is generated from a dataset of 178 H&E stained tissue cores, corresponding to 178 different patients. The data set, in this embodiment, is acquired from two independent and well-characterized collections of NSCLC represented in TMAs. The TMAs were digitally scanned at 20× magnification. Each tissue core was digitized within an image with dimensions of 1500 pixels by 1500 pixels, and labeled either "recurrence" or "non-recurrence", where information indicating recurrence or non-recurrence was acquired from the patient record. Other labeling schemes may be employed.

Embodiments may determine whether an NSCLC case represented in a TMA has recurrence or not, or whether it is likely or unlikely the region of tissue will experience recurrence. Embodiments may be evaluated in terms of ability to determine whether a NSCLC case experiences recurrence. For example, the dataset of 178 H&E stained tissue cores, corresponding to 178 different patients described above may be randomly split into a learning (i.e., training) set (n=100), and testing set (n=78). In this example, the learning set is used to determine clustering parameters and train a linear discriminant analysis (LDA) classifier model that separates cases into two classes: recurrence and non-recurrence. Unlike existing approaches, embodiments, when training the classifier, explore the features actually present in the training imagery, extract the features, and find the optimal distribution of clusters and apply that distribution of clusters to the testing set, without restricting cluster formation.

In this example, different a values may be used for generating different numbers of clusters, and the performance of each set of clusters is assessed. Additionally, embodiments are compared against two different approaches. The first existing approach employs a model in which images are characterized by lymphocyte local and contextual features but with no clustering. In this first existing approach, features pertaining to lymphocyte mean, variance, skewness, and kurtosis are used to build a feature vector. A second, different existing approach includes a prediction model constructed based on the density of TILs in an image, i.e., the ratio between the number of extant lymphocytes to the total tissue area. Embodiments predict recurrence with greater accuracy than at least these two different existing approaches.

Figure 3:
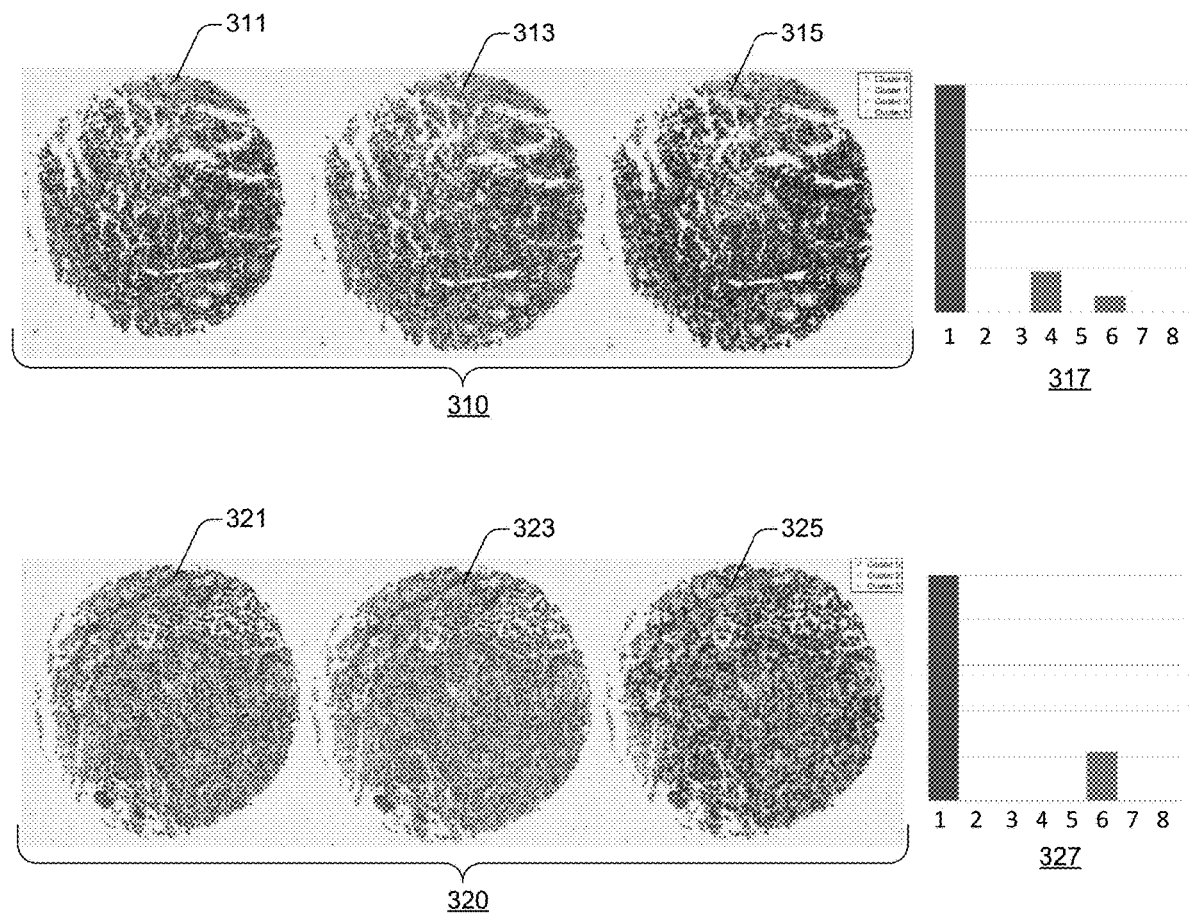
FIG. 3 illustrates regions of tissue and histograms for non-recurrence cases of lung cancer.
Figure 4:
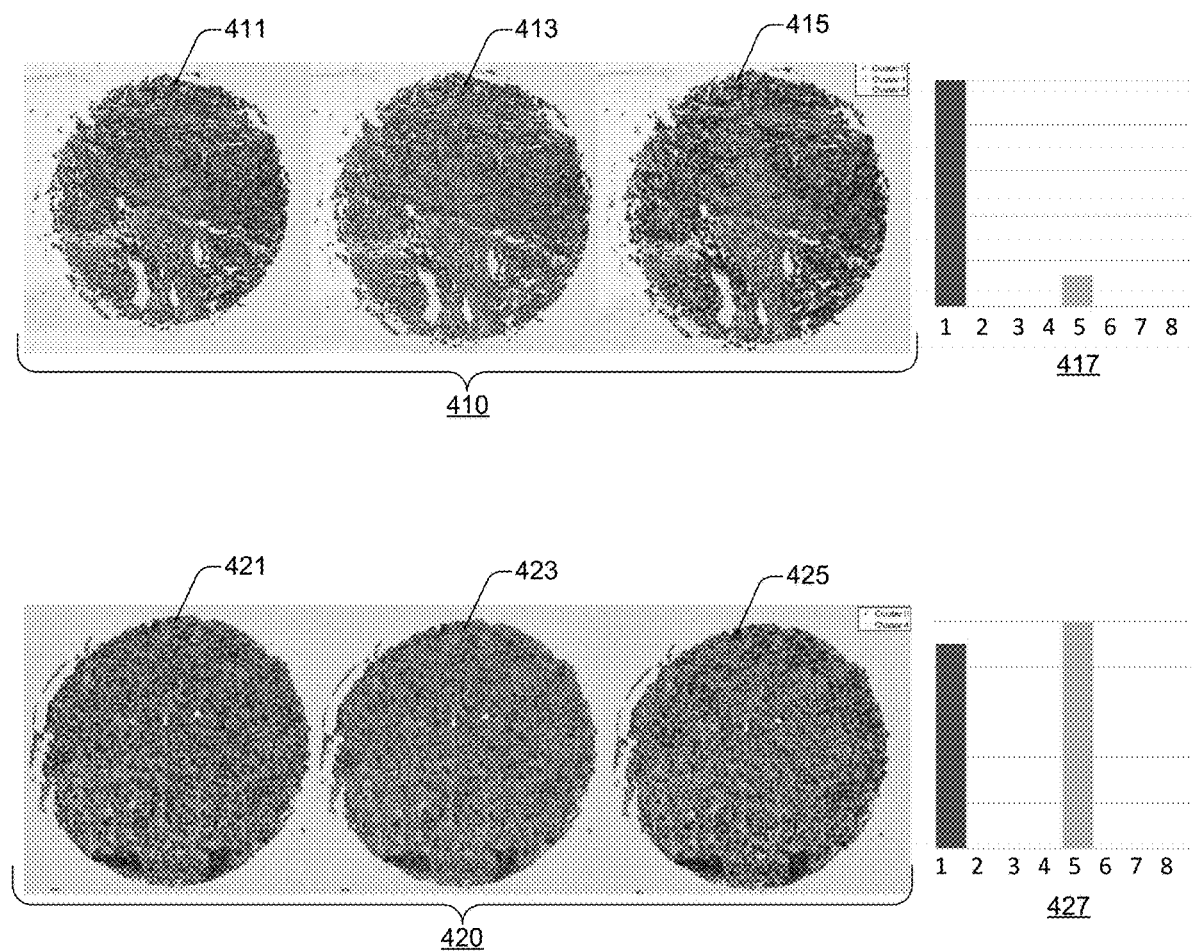
FIG. 4 illustrates regions of tissue and histograms for recurrence cases of lung cancer.

FIG. 3 illustrates visual results corresponding to two lung cancer non-recurrence cases in row 310 and row 320. Original images are illustrated at 311 and 321. 313 and 323 illustrate the original images 311 and 321 following TIL identification. TIL clustering for eight clusters is illustrated at 315 and 325. Corresponding histograms are illustrated at 317 and 327. FIG. 4 illustrates visual results corresponding to two lung cancer recurrence cases in row 410 and row 420. Original images are illustrated at 411 and 421. 413 and 423 illustrate the original images 411 and 421 following TIL identification. TIL clustering for eight clusters is illustrated at 415 and 425. Corresponding histograms are illustrated at 417 and 427. As indicated by FIG. 3 and FIG. 4, some lymphocyte populations appear more frequently on the recurrence cases (e.g., row 310 and row 320), while other, different lymphocyte populations are more common in non-recurrence cases (e.g., row 410, and row 420), the different frequency distributions demonstrated by histograms 317, 327, 417, and 427.

Figure 5:
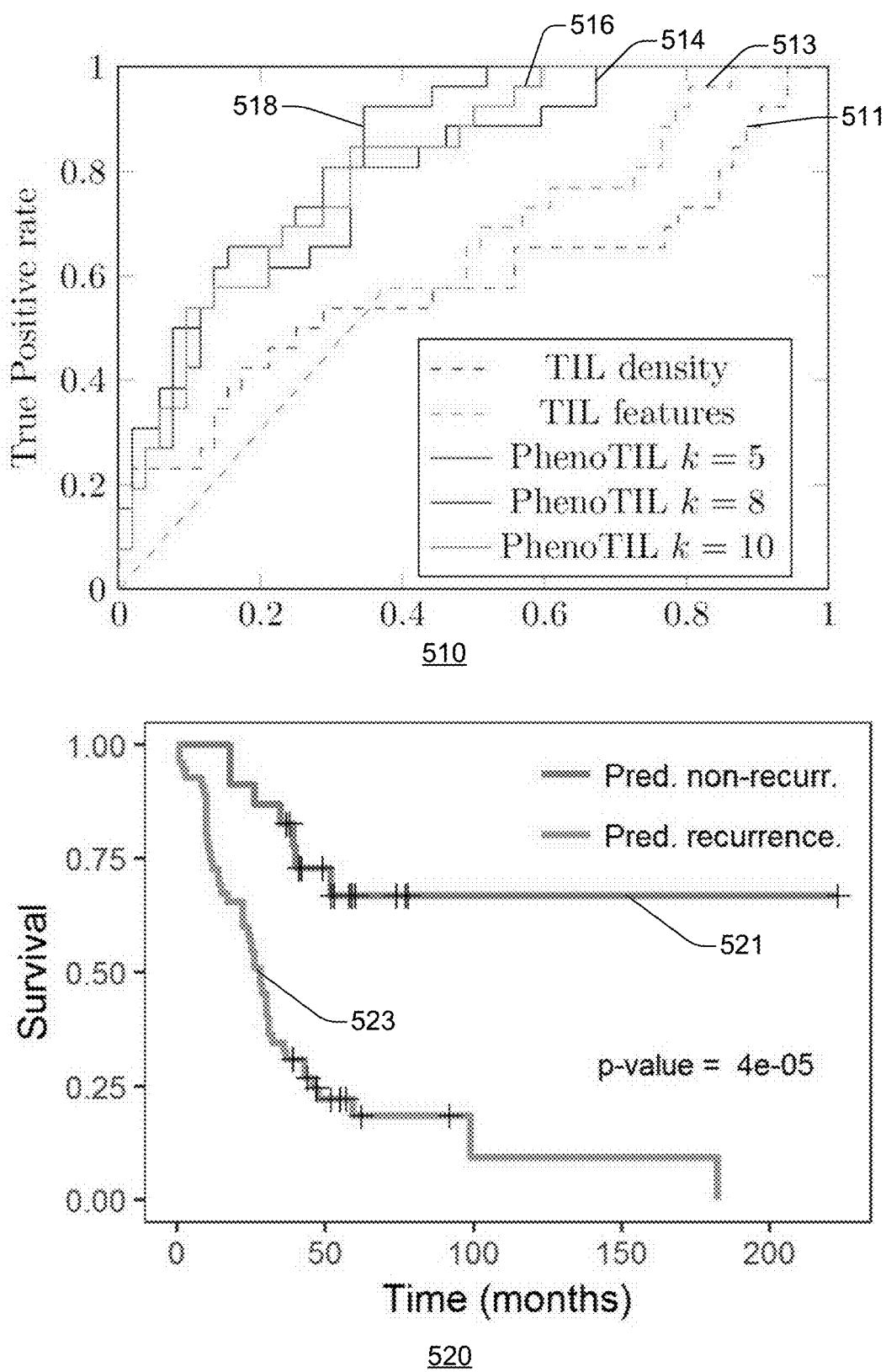
FIG. 5 illustrates Receiver Operating Characteristic (ROC) curves for existing approaches and for embodiments described herein.

FIG. 5 illustrates, at 510, Receiver Operating Characteristic (ROC) curves 511 and 513 corresponding to an existing model for predicting recurrence using only TIL density without clustering at 511, and an existing model for predicting recurrence using only local and contextual TIL features at 513. FIG. 5, at 510, further illustrates ROC curves 514, 516, and 518 for a model according to embodiments described herein that uses different a values, which results in five, eight, and ten clusters respectively. The corresponding area under the curve (AUC)s are 0.58 for the existing model for predicting recurrence using only TIL density without clustering, 0.61 for the existing model for predicting recurrence using only local and contextual TIL features, and 0.80, 0.84, and 0.81, for a model according to embodiments using five, eight, and ten clusters respectively. FIG. 5 illustrates that embodiments outperform other approaches that use other models, and that, in this example, a total of eight clusters results in the highest area under the curve.

FIG. 5 further illustrates, at 520, a Kaplan-Meier survival curve of embodiments that employ eight clusters. The curve for non-recurrence is illustrated at 521, and the curve for recurrence is illustrated at 523. Employing the previously optimally determined number of clusters (e.g., eight, in this example), embodiments may lock down the LDA classifier for survival analysis on the test set. Embodiments thus provide a highly statistically significant separation between patients who do have recurrence following surgery, and patients who do not experience recurrence following surgery.

Embodiments provide a highly statistically significant separation between patients who did and did not have recurrence following surgery. Embodiments predict recurrence in NSCLC with an AUC of at least 0.84, which is a measurable improvement over existing approaches that consider only TIL density, which achieve an AUC of only 0.54. Additionally, embodiments distinguish early recurrence from late recurrence with a statistically significant p value of $p=4\times10^{-5}$. Embodiments thus provide the technical effect of providing improved accuracy in systems, apparatus, processors, computers, or other implementations that predict recurrence based on TIL phenotyping in H&E stained images of tissue demonstrating cancerous pathology. Embodiments provide the further technical effect of providing improved recurrence prediction without the tissue destruction that existing approaches cause.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 6:
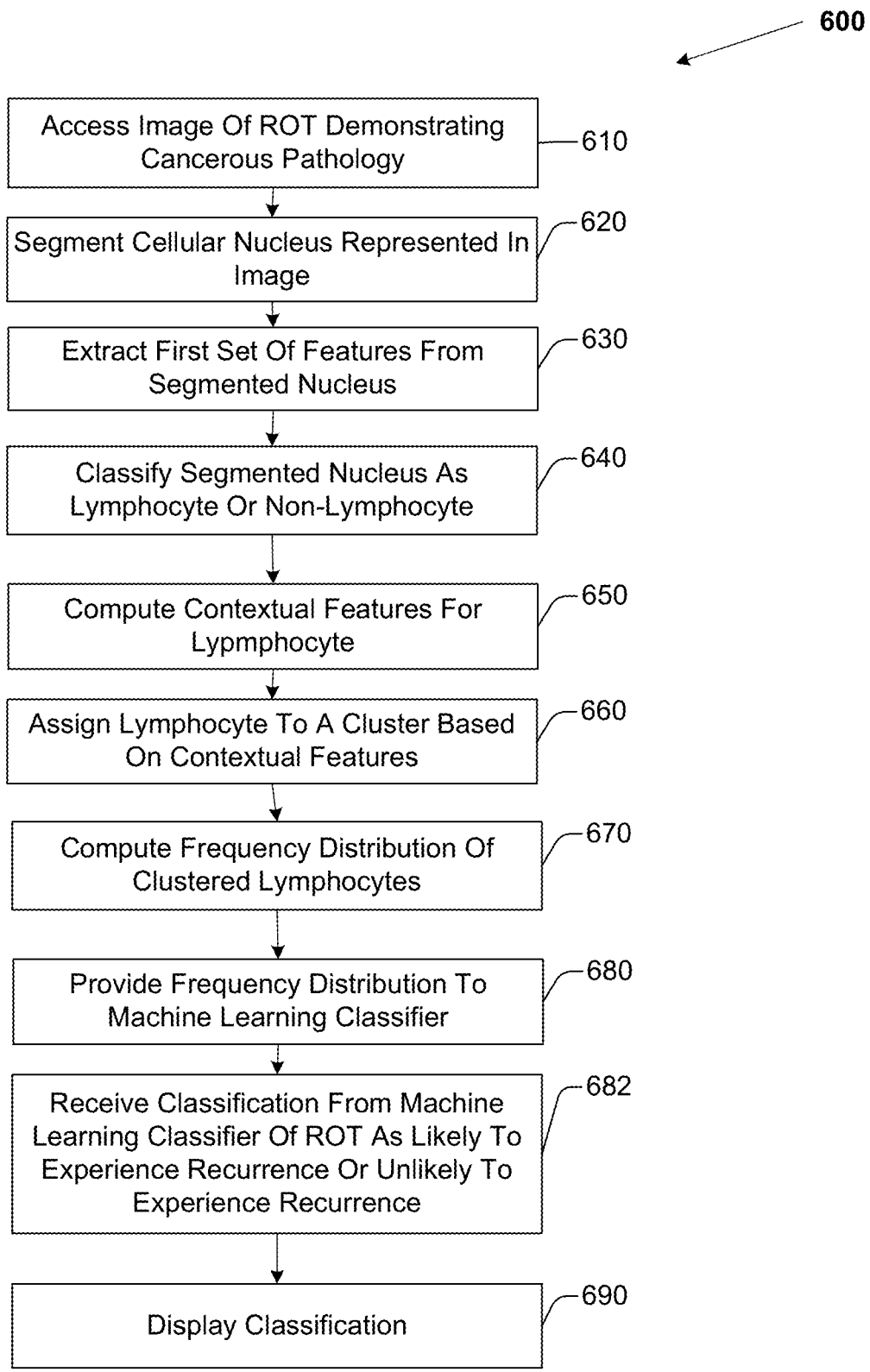
FIG. 6 illustrates a flow diagram of example operations for predicting recurrence in lung cancer.

FIG. 6 is a flow diagram of example operations 600 that may be performed by a processor for predicting recurrence in lung cancer. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 600 includes, at 610, accessing an image of a region of tissue demonstrating cancerous pathology. The image includes a plurality of pixels, a pixel having an intensity. In one embodiment, the image is a digitized image of an H&E stained tissue core scanned at 20× magnification. The image may have dimensions of 1500 pixels by 1500 pixels. In another embodiment, the image may be a digitized image of a region of tissue stained with another, different stain. In another embodiment, the image may be scanned at a different magnification (e.g., 40×), or may have other, different dimensions. Accessing the image includes acquiring electronic data, reading from a computer file, receiving a computer file, reading from a computer memory, or other computerized activity not practically performed in the human mind.

The set of operations 600 also includes, at 620 segmenting a cellular nucleus represented in the image. In one embodiment, the cellular nucleus is automatically segmented using a watershed approach. In another embodiment, other automated segmentation techniques may be employed. For example deformable based segmentation approaches, thresholding techniques, or deep learning based strategies may be employed. In another embodiment, the image accessed at 610 may already have had a cellular nucleus segmented (e.g., by another system, or by a human pathologist). Thus, in one embodiment, for an image accessed at 610 that already has a cellular nucleus segmented, step 620 may be skipped.

The set of operations 600 also includes, at 630, extracting a first set of features from the segmented cellular nucleus. In one embodiment, the first set of features includes a texture feature, a shape feature, or a color feature. In another embodiment, the first set of features may include other different features. For example, the first set of texture features may further include texture features extracted from a region immediately outside a lymphocyte (i.e., from within a threshold distance of a lymphocyte boundary). Extracting the first set of features includes acquiring electronic data, reading from a computer file, receiving a computer file, reading from a computer memory, or other computerized activity not practically performed in the human mind.

The set of operations 600 also includes, at 640, classifying the segmented nucleus as a lymphocyte or non-lymphocyte. Embodiments classify the segmented nucleus as a lymphocyte or non-lymphocyte based on the first set of features. In another embodiment, other classification schemes may be employed. For example, a different classification scheme may classify segmented nuclei as lymphocyte or non-lymphocyte when the values of the first set of features are within a threshold range, or may classify the segmented nuclei as "unknown" when the values of the first set of features are outside the threshold range.

The set of operations 600 also includes, at 650, for a segmented nucleus classified as a lymphocyte: computing a set of contextual features. In one embodiment, the set of contextual features is computed using a concentric circles method. For example, for a segmented nucleus classified as a lymphocyte, a set of circles with incremental radii of k=dL×10, dL×20, dL×30 pixels may be defined about the lymphocyte center, where dL=20 pixels is the average diameter of the detected lymphocytes. Other incremental radii values, or numbers of incremental radii, may be employed. Computing a set of contextual features includes acquiring electronic data, reading from a computer file, receiving a computer file, reading from a computer memory, or other computerized activity not practically performed in the human mind.

In one embodiment, the set of contextual features includes at least one of: a sum of an inverse Euclidean distance between the lymphocyte and another, different lymphocyte located within a concentric circle centered on the lymphocyte; a ratio between the sum of the area of lymphocytes represented within the concentric circle and the area of non-lymphocytes represented within the concentric circle; a ratio between the sum of the areas of lymphocytes represented within the concentric circle and eosinophilic tissue area represented within the concentric circle; a ratio between the number of lymphocytes represented within the concentric circle and the number of non-lymphocytes represented within the concentric circle; an average of the squared differences between the median intensities of lymphocytes represented within the concentric circle; a ratio between the area of a convex hull containing all the lymphocytes represented within the concentric circle and a convex hull containing non-lymphocytes represented within the concentric circle; an intersection between the convex hull containing all the lymphocytes represented within the concentric circle and the convex hull containing all the non-lymphocytes; a median of distances from each lymphocyte represented within the concentric circle to each lymphocyte's closest non-lymphocyte neighbor, respectively; a ratio between the median of the distance between all the lymphocytes represented within the concentric circle and their closest lymphocyte neighbor, respectively, and the median of the distance between all the non-lymphocytes represented within the concentric circle and their closest non-lymphocyte neighbor, respectively; a number of lymphocytes within a convex hull of non-lymphocytes; or a sum of distances between the centered lymphocyte and its non-lymphocytes neighbors. In another embodiment, the set of contextual features may include other, different features. In another embodiment, the set of contextual features may further include local morphological features.

The set of operations 600 also includes, at, 660, assigning the segmented nucleus classified as a lymphocyte to one of a plurality of clusters. Embodiments assign the segmented nucleus to one of a plurality of clusters based, at least in part, on the set of contextual features. In one embodiment, the segmented nucleus classified as a lymphocyte is assigned to one of the plurality of clusters based on the set of contextual features using a Dirichlet Process Gaussian Mixture Model (DPGMM). In this embodiment, the DPGMM assigns the segmented nucleus classified as a lymphocyte to a cluster using a "stick breaking" approach as described herein. In another embodiment, the segmented nucleus classified as a lymphocyte is assigned to one of the plurality of clusters using another, different clustering approach. For example, a mean-shift, graph cuts, or normalized cuts-based clustering approach may be employed. Assigning the segmented nucleus classified as a lymphocyte to a cluster includes acquiring electronic data, reading from a computer file, receiving a computer file, reading from a computer memory, or other computerized activity not practically performed in the human mind.

In one embodiment, the plurality of clusters includes eight clusters. In another embodiment, the plurality of clusters may include another, different number of clusters (e.g., five clusters, ten clusters). For example, the number of clusters may be determined based on the performance of a classifier using different values of $\alpha$, where $\alpha$ is used for generating different numbers of clusters.

The set of operations 600 also includes, at 670, computing a frequency distribution of the clustered segmented nuclei classified as lymphocytes. In one embodiment, the frequency distribution is represented as a histogram of occurrences of the clustered lymphocytes. In another embodiment, the frequency distribution may be represented using other, different statistical techniques.

The set of operations 600 also includes, at 680, providing the frequency distribution to a machine learning classifier. The set of operations 600 also includes, at 682, receiving, from the machine learning classifier, a classification of the region of tissue as likely to experience recurrence or unlikely to experience recurrence. The machine learning classifier computes the classification based, at least in part, on the frequency distribution. In one embodiment, the machine learning classifier is a linear discriminant analysis (LDA) classifier trained to classify the region of tissue as likely to experience recurrence or unlikely to experience recurrence. In another embodiment, the machine learning classifier is another type of machine learning classifier or deep learning classifier. For example, in one embodiment, the machine learning classifier may be a quadratic discriminant analysis (QDA) classifier, a random forests classifier, or a support vector machine (SVM). In another embodiment, the machine learning classifier may be a deep learning classifier, including a convolutional neural network (CNN). Other machine learning techniques may be employed to classify the region of tissue. Embodiments classify the region of tissue with an AUC of at least 0.84. Computing the classification, or receiving, from the machine learning classifier, the classification, includes acquiring electronic data, reading from a computer file, receiving a computer file, reading from a computer memory, or other computerized activity not practically performed in the human mind.

The set of operations 600 further include, at 690, displaying the classification. Displaying the classification may include displaying the classification on a computer monitor, a smartphone display, a tablet display, or other displays. Displaying the classification may also include printing the classification. Displaying the classification may also include controlling a NSCLC recurrence prediction system, a TIL phenotyping system, a monitor, or other display, to display operating parameters or characteristics of a machine learning classifier, during both training and testing, or during clinical operation of the machine learning classifier. By displaying the classification or operating parameters or characteristics of the machine learning classifier, example embodiments provide a timely and intuitive way for predicting NSCLC recurrence in a non-tissue destructive manner, thus improving on existing approaches to predicting NSCLC recurrence. Embodiments may further display the image, a segmented cellular nucleus, the first set of features, the set of contextual features, or the frequency distribution.

In one embodiment, the operations 600 further include training the machine learning classifier. In this embodiment, the machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which features extracted from a segmented nucleus, which contextual features, or which number of clusters, is most discriminative in distinguishing a positive class from a negative class (e.g., likely to experience recurrence, unlikely to experience recurrence). In one embodiment, for a first machine learning classifier, supervised learning techniques may be employed. In another embodiment, for second, different machine learning classifier, unsupervised learning techniques may be employed.

While FIG. 6 illustrates various actions occurring in serial, it is to be appreciated that various actions illustrated in FIG. 6 could occur substantially in parallel. By way of illustration, a first process could involve segmenting a cellular nucleus, a second process could involve extracting a first set of features, and a third process could involve displaying the classification. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 600, method 1000, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved, non-destructive prediction of recurrence in NSCLC may produce the technical effect of improving patient outcomes, by more accurately predicting which patients will experience recurrence. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted, when regions of tissue demonstrating NSCLC are more accurately and more quickly analyzed. Controlling an NSCLC recurrence prediction apparatus based on improved, non-destructive, more accurate prediction of NSCLC recurrence further improves the operation of the system, processor, or apparatus, since the accuracy of the system, processor, or apparatus is increased and unnecessary operations will not be performed. Embodiments described herein, including at least operations 600, apparatus 700 and 800, or method 1000, resolve features extracted from digitized H&E imagery at a higher order or higher level than a human can resolve in the human mind or with pencil and paper. For example, the average of the squared differences between the median intensities of lymphocytes, or the sum of the inverse Euclidean distances between a lymphocyte on the center of a circle and the other lymphocytes in the circled area, are not properties of a region of tissue that a human eye can perceive, nor can their extraction from a digitized image stored in computer memory be practically performed in the human mind. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Figure 7:
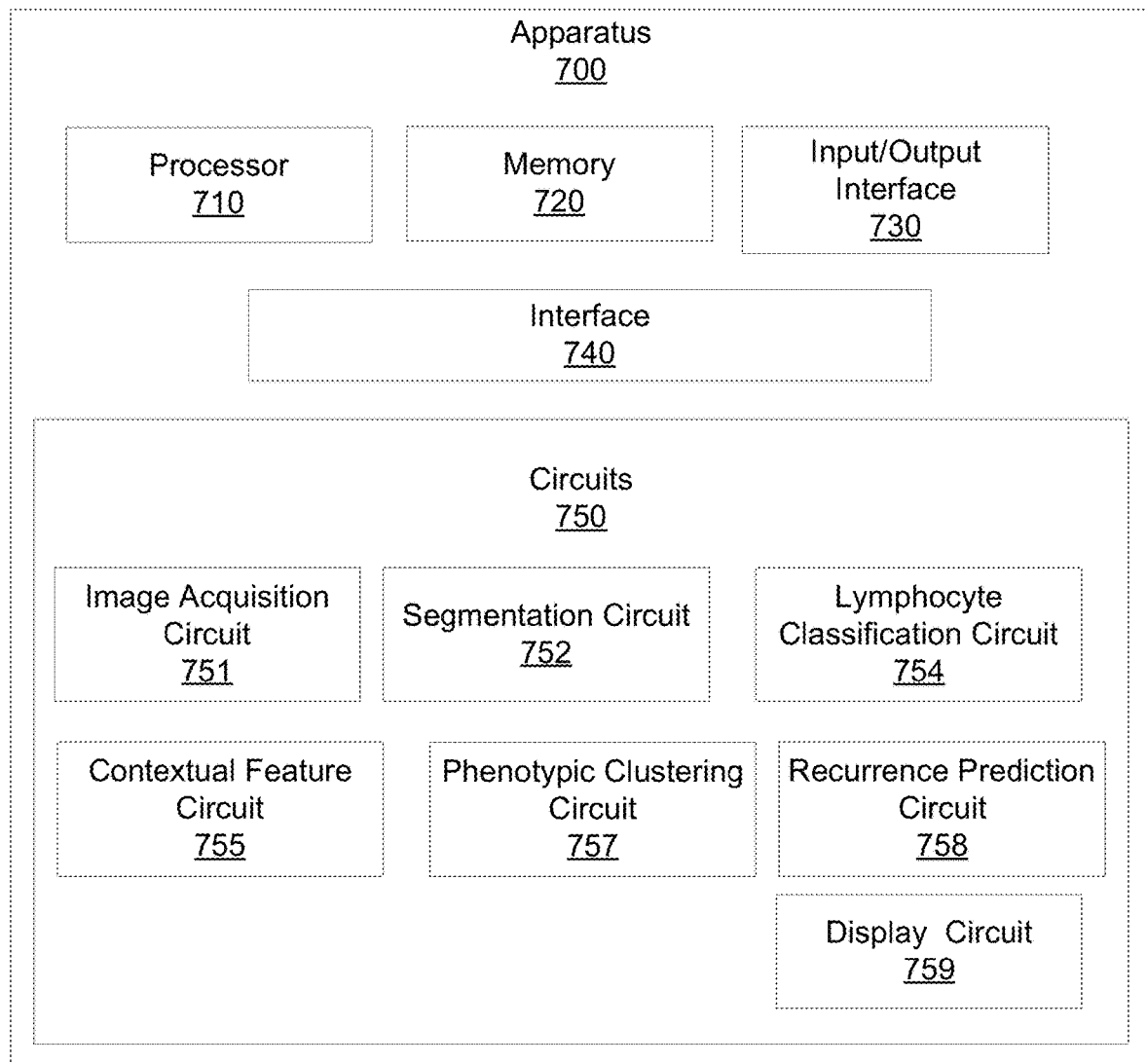
FIG. 7 illustrates an example apparatus for predicting recurrence in lung cancer.

FIG. 7 illustrates an example apparatus 700. Apparatus 700 may be configured for predicting recurrence in NSCLC, including early stage NSCLC. Apparatus 700 includes a processor 710. Apparatus 700 also includes a memory 720. Processor 710 may, in one embodiment, include circuitry such as, but not limited to, one or more single-core or multi-core processors. Processor 710 may include any combination of general-purpose processors and dedicated processors (e.g., graphics processors, application processors, etc.). The processors may be coupled with or may include memory (e.g. memory 720) or storage and may be configured to execute instructions stored in the memory 720 or storage to enable various apparatus, applications, or operating systems to perform the operations. Memory 720 is configured to store a digitized image of a region of tissue demonstrating cancerous pathology. The digitized image has a plurality of pixels, a pixel having an intensity. Memory 720 may be further configured to store a training set that includes a plurality of digitized images of regions of tissue that demonstrate cancerous pathology, where a first member of the training set includes an image of a region of tissue that experienced recurrence, and a second, different member of the training set includes an image of a region of tissue that did not experience recurrence. Memory 720 may be further configured to store a testing set that includes a plurality of digitized images of regions of tissue that demonstrate cancerous pathology, where a first member of the training set includes an image of a region of tissue that experienced recurrence, and a second, different member of the training set includes a region of tissue that did not experience recurrence.

Apparatus 700 also includes an input/output (I/O) interface 730, a set of circuits 750, and an interface 740 that connects the processor 710, the memory 720, the I/O interface 730, and the set of circuits 750. I/O interface 730 may be configured to transfer data between memory 720, processor 710, circuits 750, and external devices, for example, a NSCLC recurrence prediction system or a digital whole slide scanner.

The set of circuits 750 includes an image acquisition circuit 751, a segmentation circuit 752, a lymphocyte classification circuit 754, a contextual feature circuit 755, a phenotypic clustering circuit 757, a recurrence prediction circuit 758, and a display circuit 759.

The image acquisition circuit 751 is configured to access an image of a region of tissue demonstrating cancerous pathology. The region of tissue includes a plurality of cellular nuclei. The image has a plurality of pixels, a pixel having an intensity. Accessing the image may include accessing a digitized image stored in memory 720. In one embodiment, accessing the image may include accessing a digitized image stored in a data storage device, including a hard disk drive, a solid state device, a tape drive, or accessing a digitized image over a local area network. Accessing the digitized image includes acquiring electronic data, reading from a computer file, receiving a computer file, reading from a computer memory, or other computerized activity that cannot be practically performed in a human mind. In one embodiment, the digitized image is a digitized image of an H&E stained tissue core demonstrating early stage NSCLC scanned at 20× magnification, where the image has dimensions of 1500 pixels by 1500 pixels. In another embodiment, other stain types, magnifications, or dimensions may be employed.

Segmentation circuit 752 is configured to segment a cellular nucleus represented in the image. In one embodiment, segmentation circuit 752 is configured to automatically segment a cellular nucleus represented in the image using a watershed approach. In another embodiment, other segmentation techniques, including deformable based segmentation approaches, thresholding techniques, or deep learning based strategies may be employed. Lymphocyte classification circuit 754 is configured to extract a first set of features from the segmented cellular nucleus. Lymphocyte classification circuit 754 is further configured to classify the segmented nucleus as a lymphocyte or non-lymphocyte based on the first set of features. In one embodiment, the first set of features includes a texture feature, a shape feature, or a color feature. In another embodiment, lymphocyte classification circuit 754 may be configured to classify the segmented nucleus according to other different, classification schemes. For example, lymphocyte classification circuit 754 may be configured to classify the segmented nucleus as "lymphocyte", "non-lymphocyte", or "unknown".

Contextual feature circuit 755 is configured to compute a set of contextual features for a segmented nucleus classified as a lymphocyte. In one embodiment, contextual feature circuit 755 is configured to compute the set of contextual features using a concentric circles method. In one embodiment, for a segmented nucleus classified as a lymphocyte, contextual feature circuit 755 is configured to define a set of circles with incremental radii of k=dL×10, dL×20, dL×30 pixels, which may be centered at the lymphocyte center, where dL=20 pixels is the average diameter of the detected lymphocytes. Other incremental radii values, or numbers of incremental radii, may be employed.

In one embodiment, the set of contextual features includes at least one of: a sum of an inverse Euclidean distance between the lymphocyte and another, different lymphocyte located within a concentric circle centered on the lymphocyte; a ratio between the sum of the area of lymphocytes represented within the concentric circle and the area of non-lymphocytes represented within the concentric circle; a ratio between the sum of the areas of lymphocytes represented within the concentric circle and eosinophilic tissue area represented within the concentric circle; a ratio between the number of lymphocytes represented within the concentric circle and the number of non-lymphocytes represented within the concentric circle; an average of the squared differences between the median intensities of lymphocytes represented within the concentric circle; a ratio between the area of a convex hull containing all the lymphocytes represented within the concentric circle and a convex hull containing non-lymphocytes represented within the concentric circle; an intersection between the convex hull containing all the lymphocytes represented within the concentric circle and the convex hull containing all the non-lymphocytes; a median of distances from each lymphocyte represented within the concentric circle to each lymphocyte's closest non-lymphocyte neighbor, respectively; a ratio between the median of the distance between all the lymphocytes represented within the concentric circle and their closest lymphocyte neighbor, respectively, and the median of the distance between all the non-lymphocytes represented within the concentric circle and their closest non-lymphocyte neighbor, respectively; a number of lymphocytes within a convex hull of non-lymphocytes; or a sum of distances between the centered lymphocyte and its non-lymphocytes neighbors. In another embodiment, the set of contextual features may include other, different contextual or local morphological features.

Phenotypic clustering circuit 757 is configured to assign, based on the set of contextual features, the segmented nucleus classified as a lymphocyte to one of a plurality of clusters. In one embodiment, phenotypic clustering circuit 757 is configured to assign, based on the set of contextual features, the segmented nucleus classified as a lymphocyte to one of a plurality of clusters using a Dirichlet Process Gaussian Mixture Model (DPGMM). In one embodiment, the plurality of clusters includes eight clusters. Phenotypic clustering circuit 757 is further configured to compute a frequency distribution of the clustered segmented nuclei classified as lymphocytes. In another embodiment, phenotypic clustering circuit 757 is configured to assign, based on the set of contextual features, the segmented nucleus classified as a lymphocyte to one of a plurality of clusters using a different clustering technique, including, for example, mean-shift, graph cuts, or normalized cuts.

Recurrence prediction circuit 758 is configured to generate a classification of the region of tissue as likely to experience recurrence or unlikely to experience recurrence. Recurrence prediction circuit 758 computes the classification based, at least in part, on the frequency distribution. In one embodiment, recurrence prediction circuit 758 is configured as a linear discriminant analysis (LDA) classifier, and computes the classification using an LDA classification approach. In another embodiment, recurrence prediction circuit 758 may be configured as another, different type of machine learning or deep learning classifier. For example, recurrence prediction circuit 758 may be configured to use a QDA classification approach, a random forests classification approach, or a SVM classification approach.

Display circuit 759 is configured to display the classification. Display circuit 759 may display the classification on a computer monitor, a smartphone display, a tablet display, or other displays. In one embodiment, display circuit 759 is further configured to display at least one of the image, the first set of features, a segmented nucleus, the set of contextual features, or the frequency distribution. Displaying at least one of the image, the first set of features, a segmented nucleus, the set of contextual features, or the frequency distribution may also include printing at least one of the image, the first set of features, a segmented nucleus, the set of contextual features, or the frequency distribution.

Figure 8:
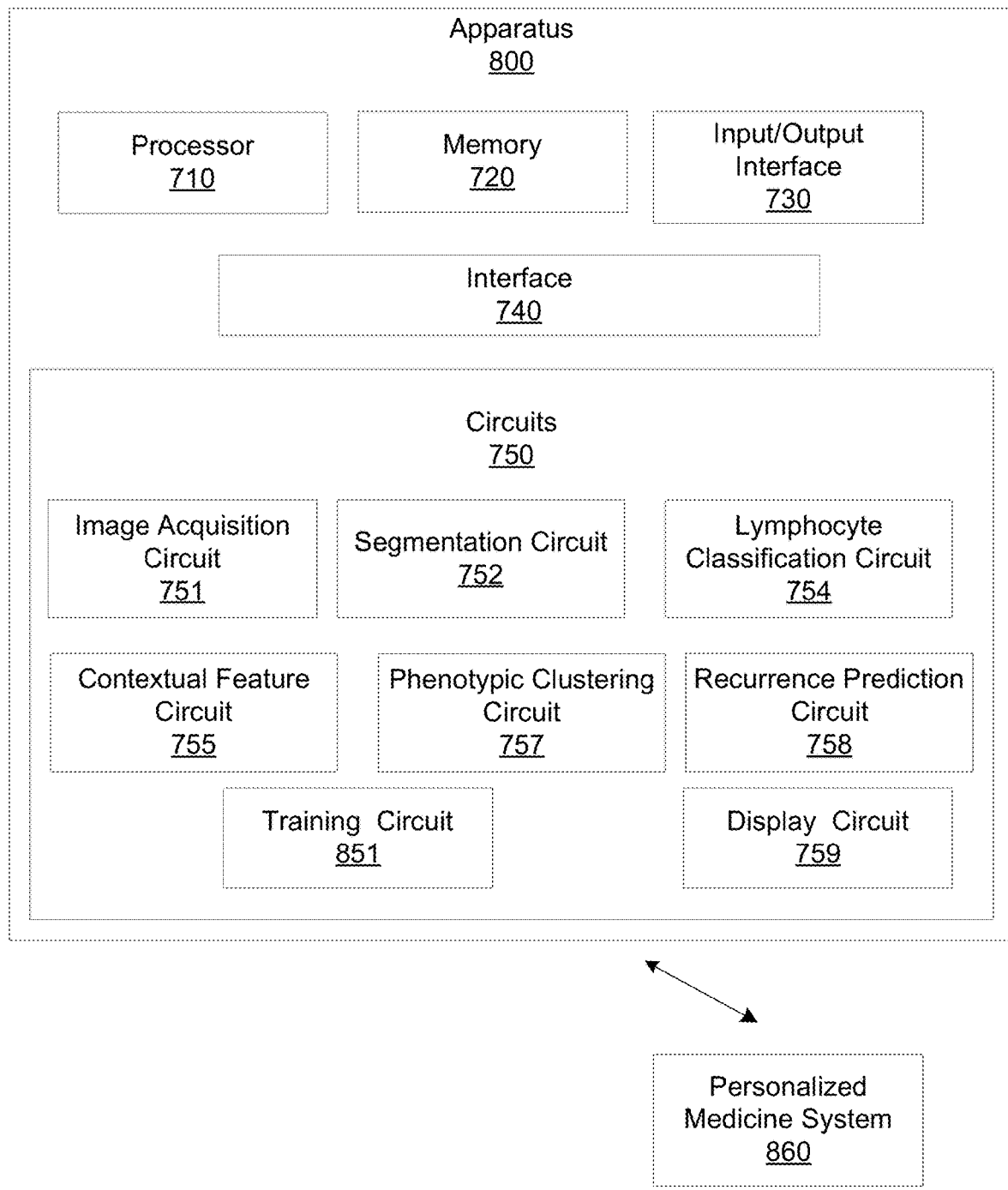
FIG. 8 illustrates an example apparatus for predicting recurrence in lung cancer.

Embodiments may include a training circuit. FIG. 8 illustrates an example apparatus 800 that is similar to apparatus 700 but that includes additional elements and details. Apparatus 800 includes a training circuit 851. Training circuit 851 may be configured to train recurrence prediction circuit 758, or other machine learning classifier, to classify an image, including a digitized H&E stained image of a region of tissue demonstrating NSCLC, according to techniques described herein. In one embodiment, the training circuit is configured to access a training dataset of images of tissue demonstrating cancerous pathology. The training dataset includes a plurality of images of tissue that experienced recurrence, and a second, different plurality of images that did not experience recurrence. The training circuit may be further configured to access a testing dataset of images, where the testing dataset includes a plurality of images of tissue that experienced recurrence, and a second, different plurality of images that did not experience recurrence. In this embodiment, the machine learning classifier is trained and tested using the training dataset and the testing dataset. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training circuit 851 may also be configured to determine which features extracted from a segmented nucleus, which contextual features, or which number of clusters, is most discriminative in distinguishing a positive class from a negative class (e.g., likely to experience recurrence, unlikely to experience recurrence).

FIG. 8 further illustrates personalized medicine system 860. Apparatus 800 may be configured to transmit the classification, the image, or other information to personalized medicine system 860. Apparatus 800 may be configured to control personalized medicine system 860 to display at least one of the image, the first set of features, a segmented nucleus, the set of contextual features, or the frequency distribution. In one embodiment, personalized medicine system 860 may be configured as a member of circuits 750. Personalized medicine system 860 may be configured to generate a personalized NSCLC treatment plan based, at least in part, on the classification. For example, personalized medicine system 860 may be configured to compute a dosage or dosage schedule of a chemotherapy agent, or an immunotherapy agent based, at least in part, on the classification. For example, for region of tissue classified as likely to experience recurrence, a first dosage schedule may be generated, while for a region of tissue classified as unlikely to experience recurrence, a second, different dosage schedule may be generated.

Figure 9:
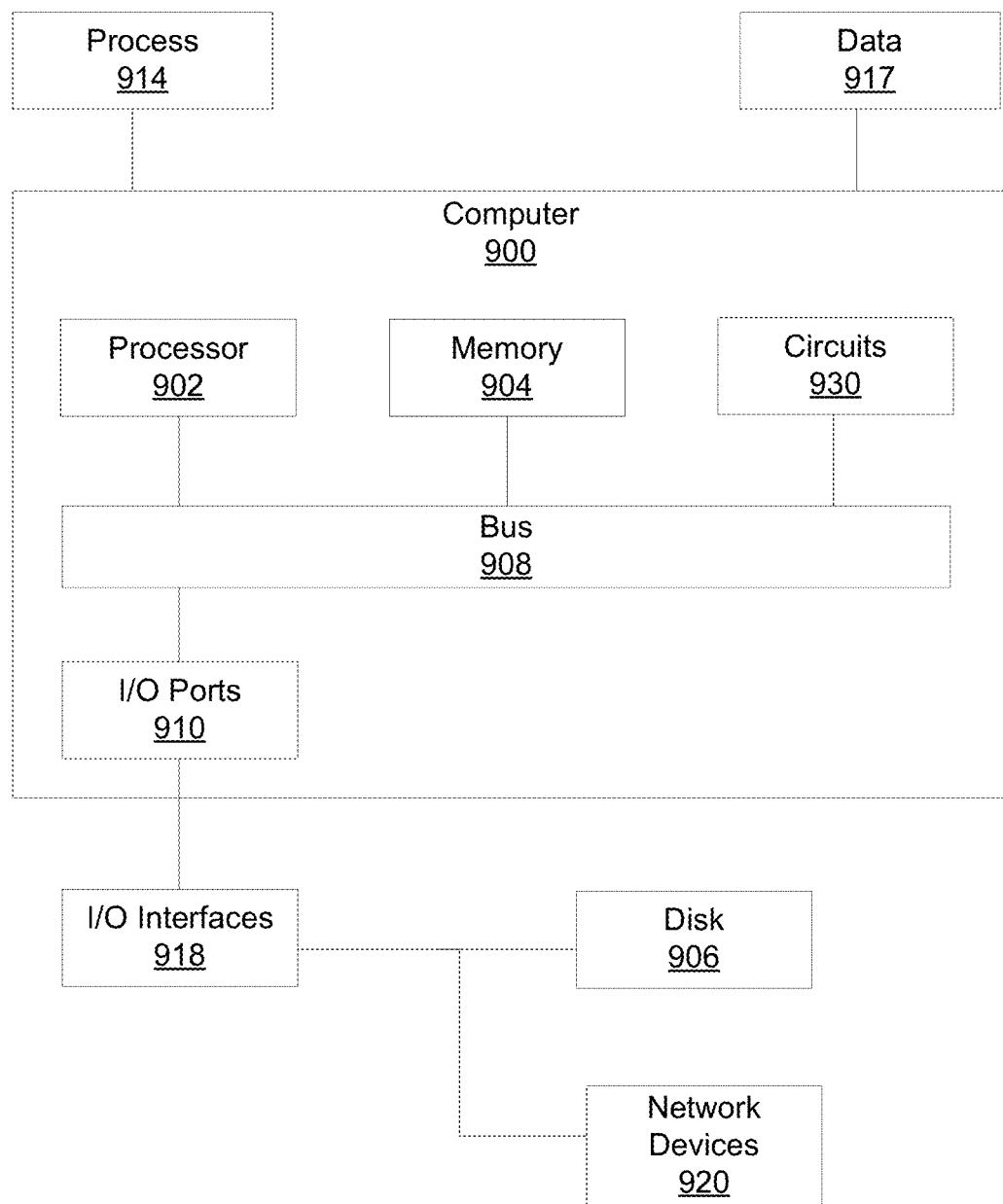
FIG. 9 illustrates an example computer in which embodiments described herein may operate.

FIG. 9 illustrates an example computer 900 in which example methods illustrated herein can operate and in which example methods, apparatus, circuits, operations, or logics may be implemented. In different examples, computer 900 may be part of a NSCLC recurrence prediction system or apparatus, a digital whole slide scanner, may be operably connectable to a NSCLC recurrence prediction system or apparatus, or a digital whole slide scanner.

Computer 900 includes a processor 902, a memory 904, and input/output (I/O) ports 910 operably connected by a bus 908. In one example, computer 900 may include a set of logics or circuits 930 that perform operations for or a method of predicting recurrence in NSCLC using a machine learning classifier. Thus, the set of circuits 930, whether implemented in computer 900 as hardware, firmware, software, and/or a combination thereof may provide means (e.g., hardware, firmware, circuits) for predicting recurrence in NSCLC. In different examples, the set of circuits 930 may be permanently and/or removably attached to computer 900.

Processor 902 can be a variety of various processors including dual microprocessor and other multi-processor architectures. Processor 902 may be configured to perform operations or steps of methods claimed and described herein. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a flash memory card, or a memory stick. Furthermore, disk 906 may include optical drives like a CD-ROM or a digital video ROM drive (DVD ROM). Memory 904 can store processes 914 or data 917, for example. Data 917 may, in one embodiment, include digitized pathology slides. Disk 906 or memory 904 can store an operating system that controls and allocates resources of computer 900.

Bus 908 can be a single internal bus interconnect architecture or other bus or mesh architectures. While a single bus is illustrated, it is to be appreciated that computer 900 may communicate with various devices, circuits, logics, and peripherals using other buses that are not illustrated (e.g., PCIE, SATA, Infiniband, 794, USB, Ethernet).

Computer 900 may interact with input/output devices via I/O interfaces 918 and input/output ports 910. Input/output devices can include, but are not limited to, CT systems, MRI systems, digital whole slide scanners, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks, including the cloud.

Figure 10:
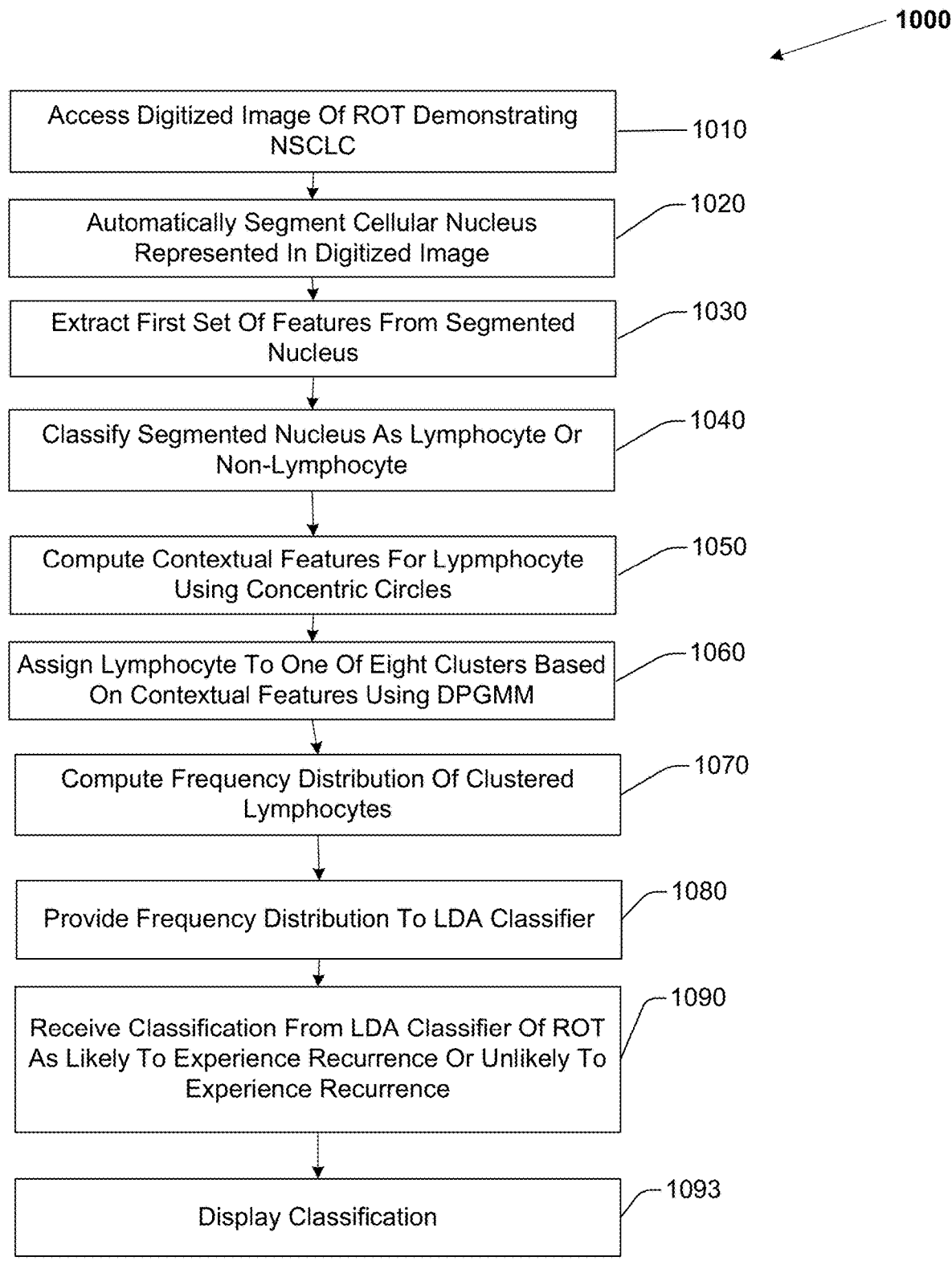
FIG. 10 illustrates an example method for predicting recurrence in lung cancer.

FIG. 10 illustrates an example method 1000. Method 1000 includes, at 1010 accessing a digitized image of a region of tissue demonstrating NSCLC. The image has a plurality of pixels, a pixel having an intensity. Accessing the digitized image includes acquiring electronic data, reading from a computer file, receiving a computer file, reading from a computer memory, or other computerized activity that cannot be practically performed in the human mind. In one embodiment, the digitized image is a digitized image of an H&E stained tissue core scanned at 20× magnification, the digitized image having dimensions of 1500 pixels by 1500 pixels. In another embodiment, other stain types, magnifications, or dimensions may be employed.

Method 1000 also includes, at 1020 automatically segmenting a cellular nucleus represented in the digitized image using a watershed segmentation approach. Automatically segmenting the cellular nucleus using a watershed segmentation approach may include acquiring electronic data, reading from a computer file, receiving a computer file, reading from a computer memory, or other computerized activity that cannot be practically performed in the human mind. In another embodiment, other segmentation techniques may be employed to automatically segment the cellular nucleus.

Method 1000 also includes, at 1030 extracting a first set of features from the segmented cellular nucleus. The first set of features includes a texture feature, a shape feature, and a color feature. Extracting the first set of features may include acquiring electronic data, reading from a computer file, receiving a computer file, reading from a computer memory, or other computerized activity that cannot be practically performed in the human mind. In another embodiment, the first set of features may include other, different features extracted from the segmented cellular nucleus.

Method 1000 also includes, at 1040, classifying the segmented nucleus as a lymphocyte or non-lymphocyte based on the first set of features. In another embodiment, the segmented cellular nucleus may be classified as, for example, "lymphocyte", "non-lymphocyte", or "unknown".

Method 1000 also includes, at 1050, for a segmented nucleus classified as a lymphocyte: computing a set of contextual features using a concentric circles approach. Computing the set of contextual features using a concentric circles approach may include acquiring electronic data, reading from a computer file, receiving a computer file, reading from a computer memory, or other computerized activity that cannot be practically performed in the human mind. Concentric circles centered on the centroid of the segmented nucleus classified as a lymphocyte may have incremental radii of k=dL×10, dL×20, dL×30 pixels, where dL=20 pixels is the average diameter of the detected lymphocytes. In another embodiment, other, different incremental radii, or numbers of incremental radii, may be employed.

Method 1000 also includes, at 1060, assigning the segmented nucleus classified as a lymphocyte to one of eight clusters based on the set of contextual features using a Dirichlet Process Gaussian Mixture Model (DPGMM) clustering approach. Assigning the segmented nucleus to a cluster using a DPGMM clustering approach includes acquiring electronic data, reading from a computer file, receiving a computer file, reading from a computer memory, or other computerized activity that cannot be practically performed in the human mind. In another embodiment, other numbers of clusters may be employed. In another embodiment, other clustering approaches may be employed.

Method 1000 also includes, at 1070, computing a frequency distribution of the clustered segmented nuclei classified as lymphocytes. In one embodiment, the frequency distribution is represented as a histogram.

Method 1000 also includes, at 1080, providing the frequency distribution to an LDA classifier. Providing the frequency distribution to the LDA classifier includes acquiring electronic data, reading from a computer file, receiving a computer file, reading from a computer memory, or other computerized activity that cannot be practically performed in the human mind.

Method 1000 also includes, at 1090, receiving, from the LDA classifier, a classification of the region of tissue as likely to experience recurrence or unlikely to experience recurrence. The LDA classifier computes the classification based, at least in part, on the frequency distribution. In another embodiment, other types of machine learning classifiers or deep learning classifiers may be employed, including a QDA classifier, a SVM classifier, or a CNN classifier.

Method 1000 further includes, at 1093 displaying the classification. Displaying the classification may include displaying the classification on a computer monitor, a smartphone display, a tablet display, or other displays. In one embodiment, further includes displaying at least one of the image, the first set of features, a segmented nucleus, the set of contextual features, or the frequency distribution.

Examples herein can include subject matter such as an apparatus, an NSCLC recurrence prediction system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting recurrence in NSCLC, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed control a processor to perform operations, the operations comprising:
   accessing an image of a region of tissue demonstrating cancerous pathology, the image including a plurality of pixels, a pixel having an intensity;
   segmenting a cellular nucleus represented in the image;
   extracting a first set of features from the segmented cellular nucleus;
   classifying the segmented cellular nucleus as a lymphocyte or non-lymphocyte based on the first set of features;
   for a segmented cellular nucleus classified as the lymphocyte:
      computing a set of contextual features;
   assigning the segmented cellular nucleus classified as the lymphocyte to one of a plurality of clusters based on the set of contextual features;
   computing a frequency distribution of the clustered segmented cellular nuclei classified as lymphocytes;
   providing the frequency distribution to a machine learning classifier;
   receiving, from the machine learning classifier, a classification of the region of tissue as likely to experience recurrence or unlikely to experience recurrence, where the machine learning classifier computes the classification based, at least in part, on the frequency distribution; and
   displaying the classification.

2. The non-transitory computer-readable storage device of claim 1, where the image is a digitized image of a hematoxylin and eosin (H&E) stained non-small cell lung cancer (NSCLC) tissue core scanned at 20× magnification, where the image has dimensions of 1500 pixels by 1500 pixels.

3. The non-transitory computer-readable storage device of claim 1, where segmenting the cellular nucleus represented in the image includes segmenting a nucleus represented in the image using a watershed approach.

4. The non-transitory computer-readable storage device of claim 1, where the first set of features includes a texture feature, a shape feature, or a color feature.

5. The non-transitory computer-readable storage device of claim 1, where the set of contextual features is extracted using a concentric circles method.

6. The non-transitory computer-readable storage device of claim 5, where the set of contextual features includes at least one of:
   a sum of an inverse Euclidean distance between the lymphocyte and another, different lymphocyte located within a concentric circle centered on the lymphocyte;
   a ratio between the sum of the area of lymphocytes represented within the concentric circle and the area of non-lymphocytes represented within the concentric circle;
   a ratio between the sum of the areas of lymphocytes represented within the concentric circle and eosinophilic tissue area represented within the concentric circle;
   a ratio between the number of lymphocytes represented within the concentric circle and the number of non-lymphocytes represented within the concentric circle;
   an average of squared differences between the median intensities of lymphocytes represented within the concentric circle;
   a ratio between the area of a convex hull containing all the lymphocytes represented within the concentric circle and a convex hull containing non-lymphocytes represented within the concentric circle;
   an intersection between the convex hull containing all the lymphocytes represented within the concentric circle and the convex hull containing all the non-lymphocytes;
   a median of distances from each lymphocyte represented within the concentric circle to each lymphocyte's closest non-lymphocyte neighbor, respectively;
   a ratio between the median of the distance between all the lymphocytes represented within the concentric circle and their closest lymphocyte neighbor, respectively, and the median of the distance between all the non-lymphocytes represented within the concentric circle and their closest non-lymphocyte neighbor, respectively;
   a number of lymphocytes within a convex hull of non-lymphocytes; or
   a sum of distances between the centered lymphocyte and its non-lymphocytes neighbors.

7. The non-transitory computer-readable storage device of claim 1, where the segmented cellular nucleus classified as the lymphocyte is assigned to one of the plurality of clusters based on the set of contextual features using a Dirichlet Process Gaussian Mixture Model clustering approach.

8. The non-transitory computer-readable storage device of claim 7, where the plurality of clusters includes eight clusters.

9. The non-transitory computer-readable storage device of claim 7, where the frequency distribution is represented as a histogram of occurrences of the clustered lymphocytes.

10. The non-transitory computer-readable storage device of claim 1, where the machine learning classifier is a linear discriminant analysis (LDA) classifier configured to classify the region of tissue as likely to experience recurrence or unlikely to experience recurrence.

11. The non-transitory computer-readable storage device of claim 10, where the LDA classifier classifies the region of tissue with an area under the receiver operating characteristic curve (AUC) of at least 0.84.

12. An apparatus for predicting disease recurrence, the apparatus comprising:
a processor;
a memory configured to store a digitized image of a region of tissue demonstrating cancerous pathology, the image including a plurality of pixels, a pixel having an intensity;
an input/output (I/O) interface;
a set of circuits; and
an interface that connects the processor, the memory, the I/O interface, and the set of circuits, the set of circuits comprising:
an image acquisition circuit configured to:
access an image of the region of tissue demonstrating cancerous pathology, where the region of tissue includes a plurality of cellular nuclei;
a segmentation circuit configured to:
segment a cellular nucleus represented in the image;
a lymphocyte classification circuit configured to:
extract a first set of features from the segmented cellular nucleus; and
classify the segmented cellular nucleus as a lymphocyte or non-lymphocyte based on the first set of features;
a contextual feature circuit configured to:
compute a set of contextual features for a segmented cellular nucleus classified as the lymphocyte;
a phenotypic clustering circuit configured to:
assign, based on the set of contextual features, the segmented cellular nucleus classified as the lymphocyte to one of a plurality of clusters; and
compute a frequency distribution of the clustered segmented cellular nuclei classified as lymphocytes;
a recurrence prediction circuit configured to:
generate a classification of the region of tissue as likely to experience recurrence or unlikely to experience recurrence, where the lymphocyte classification circuit computes the classification based, at least in part, on the frequency distribution; and
a display circuit configured to display the classification.

13. The apparatus of claim 12, where the digitized image is a digitized image of a hematoxylin and eosin (H&E) stained tissue core demonstrating early stage non-small cell lung cancer (NSCLC) scanned at 20× magnification, where the image has dimensions of 1500 pixels by 1500 pixels.

14. The apparatus of claim 12, where the segmentation circuit is configured to segment the cellular nucleus represented in the image using a watershed approach.

15. The apparatus of claim 12, where the first set of features includes a texture feature, a shape feature, or a color feature.

16. The apparatus of claim 12, where the contextual feature circuit is configured to extract the set of contextual features using a concentric circles method.

17. The apparatus of claim 16, where the set of contextual features includes at least one of:
a sum of an inverse Euclidean distance between the lymphocyte and another, different lymphocyte located within a concentric circle centered on the lymphocyte;
a ratio between the sum of the area of lymphocytes represented within the concentric circle and the area of non-lymphocytes represented within the concentric circle;
a ratio between the sum of the areas of lymphocytes represented within the concentric circle and eosinophilic tissue area represented within the concentric circle;
a ratio between the number of lymphocytes represented within the concentric circle and the number of non-lymphocytes represented within the concentric circle;
an average of squared differences between the median intensities of lymphocytes represented within the concentric circle;
a ratio between the area of a convex hull containing all the lymphocytes represented within the concentric circle and a convex hull containing non-lymphocytes represented within the concentric circle;
an intersection between the convex hull containing all the lymphocytes represented within the concentric circle and the convex hull containing all the non-lymphocytes;
a median of distances from each lymphocyte represented within the concentric circle to each lymphocyte's closest non-lymphocyte neighbor, respectively;
a ratio between the median of the distance between all the lymphocytes represented within the concentric circle and their closest lymphocyte neighbor, respectively, and the median of the distance between all the non-lymphocytes represented within the concentric circle and their closest non-lymphocyte neighbor, respectively;
a number of lymphocytes within a convex hull of non-lymphocytes; or
a sum of distances between the centered lymphocyte and its non-lymphocytes neighbors.

18. The apparatus of claim 13, where the phenotypic clustering circuit is configured to assign, based on the set of contextual features, the segmented cellular nucleus classified as the lymphocyte to one of a plurality of clusters using a Dirichlet Process Gaussian Mixture Model (DPGMM) clustering approach.

19. The apparatus of claim 13, where the recurrence prediction circuit is further configured to generate the classification using a linear discriminant analysis (LDA) classification approach.

20. A non-transitory computer-readable storage device storing computer-executable instructions that when executed control a computer to perform a method of predicting recurrence in non-small cell lung cancer (NSCLC), the method comprising:
accessing a digitized image of a region of tissue demonstrating NSCLC, the image having a plurality of pixels, a pixel having an intensity;
automatically segmenting a cellular nucleus represented in the digitized image using a watershed segmentation approach;
extracting a first set of features from the segmented cellular nucleus, where the first set of features includes a texture feature, a shape feature, and a color feature;
classifying the segmented cellular nucleus as a lymphocyte or non-lymphocyte based on the first set of features;
for a segmented cellular nucleus classified as the lymphocyte:
computing a set of contextual features using a concentric circles approach;
assigning the segmented cellular nucleus classified as the lymphocyte to one of eight clusters based on the set of contextual features using a Dirichlet Process Gaussian Mixture Model (DPGMM) clustering approach;
computing a frequency distribution of the clustered segmented cellular nuclei classified as lymphocytes;
providing the frequency distribution to a linear discriminant analysis (LDA) classifier;

receiving, from the LDA classifier, a classification of the region of tissue as likely to experience recurrence or unlikely to experience recurrence, where the LDA classifier computes the classification based, at least in part, on the frequency distribution; and
displaying the classification.

\* \* \* \* \*